(12) United States Patent
Cho et al.

(10) Patent No.: US 11,547,360 B2
(45) Date of Patent: Jan. 10, 2023

(54) ACUTE HEART FAILURE MONITORING AND TREATMENT

(71) Applicant: Medtronic, Inc., Minneapolis, MN (US)

(72) Inventors: Yong K. Cho, Excelsior, MN (US); Tom D. Bennett, Shoreview, MN (US); Douglas A. Hettrick, Andover, MN (US); Charles P. Sperling, Edina, MN (US); Paul A. Sobotka, West St. Paul, MN (US); Vinod Sharma, Maple Grove, MN (US); Eduardo N. Warman, Maple Grove, MN (US); Todd M. Zielinski, Ham Lake, MN (US)

(73) Assignee: MEDTRONIC, INC., Minneapolis, MN (US)

(*) Notice: Subject to any disclaimer, the term of this patent is extended or adjusted under 35 U.S.C. 154(b) by 466 days.

(21) Appl. No.: 16/723,828

(22) Filed: Dec. 20, 2019

(65) Prior Publication Data
US 2020/0196948 A1    Jun. 25, 2020

Related U.S. Application Data

(60) Provisional application No. 62/783,728, filed on Dec. 21, 2018.

(51) Int. Cl.
*A61B 5/00*    (2006.01)
*A61B 5/107*    (2006.01)
*A61B 5/029*    (2006.01)

(52) U.S. Cl.
CPC .............. *A61B 5/686* (2013.01); *A61B 5/029* (2013.01); *A61B 5/1073* (2013.01); *A61B 5/6869* (2013.01); *A61B 5/6876* (2013.01)

(58) Field of Classification Search
CPC ... A61B 5/0537; A61B 5/0538; A61B 5/0809; A61B 5/4035; A61B 5/4869;
(Continued)

(56) References Cited

U.S. PATENT DOCUMENTS 6,473,640 B1    10/2002    Erlebacher
6,887,207 B2    5/2005    Hettrick
(Continued)

FOREIGN PATENT DOCUMENTS

WO    2018/023132    2/2018

OTHER PUBLICATIONS

International Preliminary Report on Patentability from PCT Application No. PCT/US2019/067884 dated Jul. 1, 2021, 9 pages.
(Continued)

*Primary Examiner* — Jon Eric C Morales
(74) *Attorney, Agent, or Firm* — Mueting Raasch Group

(57) ABSTRACT

Systems and methods include differential diagnosis for acute heart failure to provide treatment to a patient including determining whether the patient has cardiac volume overload, determining whether the patient has decreased abdominal venous system volume, and providing the appropriate treatment in response to the determinations. A multi-sensor system may be used to determine cardiac volume and abdominal venous system volume. Fluid redistribution treatment may be provided when cardiac volume overload is accompanied by a decrease in abdominal venous system volume. Fluid accumulation treatment may be provided when cardiac volume overload is not accompanied by a decrease in abdominal venous system volume.

21 Claims, 5 Drawing Sheets

(58) Field of Classification Search
CPC .............. A61N 1/3601; A61N 1/36114; A61N 1/36521; A61N 1/36585
See application file for complete search history.

(56) References Cited

U.S. PATENT DOCUMENTS

| | | |
|---|---|---|
| 7,387,610 B2 | 6/2008 | Stahmann et al. |
| 7,881,781 B2 | 2/2011 | Stahmann et al. |
| 7,986,994 B2 | 7/2011 | Stadler et al. |
| 8,255,046 B2 | 8/2012 | Sarkar et al. |
| 8,483,821 B2 | 7/2013 | Averina et al. |
| 8,868,185 B2 | 10/2014 | Zielinski et al. |
| 2010/0004714 A1 | 1/2010 | Georgakopoulos et al. |
| 2010/0113888 A1 | 5/2010 | Cho et al. |
| 2011/0022127 A1* | 1/2011 | Averina ............. A61N 1/36585 607/62 |
| 2018/0168468 A1 | 6/2018 | Kelly et al. |

OTHER PUBLICATIONS

Martens et al., "How to tackle congesting in acute heart failure", Korean Journal of Internal Medicine, vol. 33, No. 3, Apr. 2018, pp. 462-473.

International Search Report and Written Opinion from PCT Application No. PCT/US2019/067884 dated April 9, 2020, 15 pages.

Cotter et al., "Fluid overload in acute heart failure—re-distribution and other mechanisms beyond fluid accumulation," Feb. 2008, *Eur J Heart Fail.*, 10:165-169.

Fallick et al., "Sympathetically mediated changes in capacitance: redistribution of the venous reservoir as a cause of decompensation," 2011, *Circulation Heart Failure*, 4:669-675.

Greenway et al., "Capacitance effects and blood reservoir function in the splanchnic vascular bed during non-hypotensive haemorrhage and blood volume expansion in anaesthetized cats," Mar. 1974, *Journal of Physiology*, 237:279-294.

Rothe, "Reflex control of veins and vascular capacitance," Oct. 1983, *Physiological Reviews*, 63:1281-1342.

* cited by examiner

ACUTE HEART FAILURE MONITORING AND TREATMENT

The present application claims the benefit of U.S. Provisional Application Ser. No. 62/783,728, filed Dec. 21, 2018, which is incorporated by reference in its entirety.

The present technology is generally related to medical systems and methods, such as acute heart failure monitoring and treatment systems and methods.

Acute heart failure (AHF), or acute decompensated heart failure (ADHF) is a common cause for hospital admission. Readmission of patients within 30-days of discharge is also a common challenge. AHF may be the result of specific disease process other than chronic heart failure (HF) in some patients, but in many cases, AHF is the culmination of worsening chronic HF. Volume overload is considered a hallmark of AHF, and many patients admitted to hospitals with AHF receive diuretic therapy, which may not be effective for all patients.

SUMMARY

The techniques of this disclosure generally relate to systems and methods for providing a differential diagnosis for acute heart failure to provide treatment to a patient. In particular, these techniques can be used to determine whether acute heart failure is caused more by fluid accumulation or by fluid redistribution, and the appropriate treatment may be provided. Various embodiments may include determining whether a patient has cardiac volume overload, determining whether a patient has decreased abdominal venous system volume, and providing the appropriate treatment in response to the determinations.

In one aspect, the present disclosure provides a method that includes determining whether a patient has cardiac volume overload; determining whether a patient has decreased abdominal venous system volume; and determining an appropriate based on determining whether the patient has cardiac volume overload and determining whether the patient has decreased abdominal venous system volume.

In another aspect, the present disclosure provides a system that includes one or both of a thoracic device having a sensor to measure cardiac volume and an abdominal device having a sensor to measure abdominal venous system volume. The system also includes a controller operably coupled to the thoracic device or the abdominal device. The controller includes a processor configured to: determine whether a patient has cardiac volume overload in response to a cardiac volume measurement; determine whether a patient has decreased abdominal venous system volume in response to an abdominal venous system volume measurement; and determine an appropriate treatment based on determining whether the patient has cardiac volume overload and determining whether the patient has decreased abdominal venous system volume.

In another aspect, the present disclosure provides a system that includes an interface to one or more thoracic devices to measure cardiac volume. The system also includes an interface to one or more abdominal devices to measure abdominal venous system volume. The system also includes an interface to one or more user interface devices. Further, the system includes a controller operably coupled to the interfaces to one or more thoracic devices and to one or more abdominal devices to receive measurements of cardiac volume and abdominal venous system volume. The controller includes a processor configured to: receive a cardiac volume using the interface to one or more thoracic devices; receive an abdominal venous system volume using the interface to one or more abdominal devices; and provide measurements of the cardiac volume and the abdominal venous system volume using the interface to one or more user interface devices.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
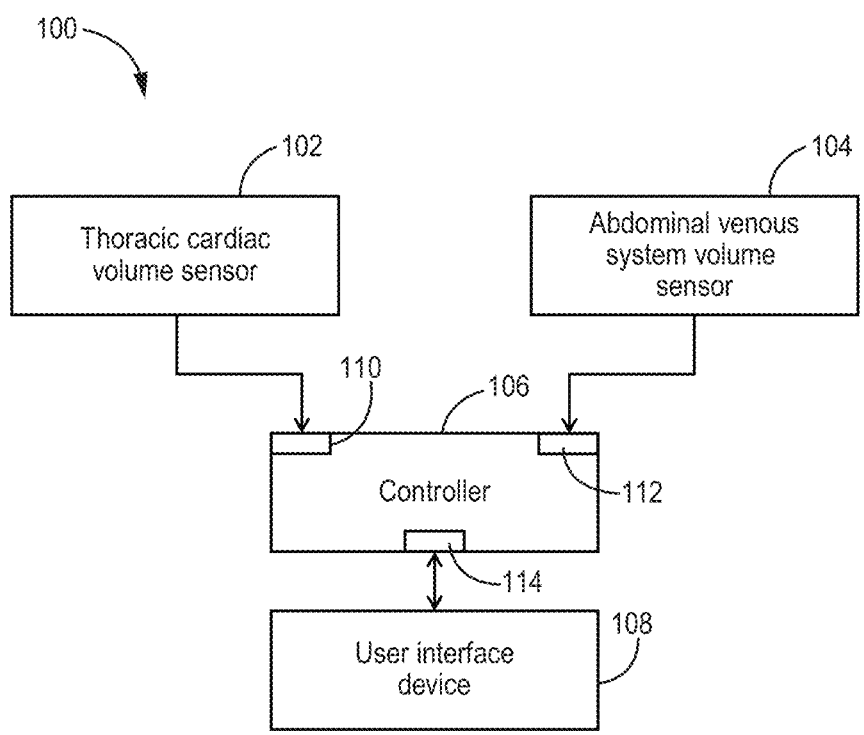
FIG. 1 is a block diagram that illustrates an acute heart failure monitoring and treatment system according to the present disclosure.

This disclosure relates to systems and methods for providing a differential diagnosis for acute heart failure to provide treatment to a patient. When a patient is admitted to a hospital for acute heart failure (AHF), the total body fluid accumulation (e.g., accompanying body weight gain) may not be the only mechanism for cardiac volume overload. Venous capacitance may be involved, especially the role of splanchnic reserve as the body's compensatory mechanism. The mechanisms for AHF may include venous capacitance change. A large portion of blood in the venous system (e.g., mainly in the splanchnic vessels) may not contribute to the effective circulating blood volume but can be recruited to the circulating blood volume with activation of the sympathetic nerve stimuli, drugs, or hormones. In patients with cardiac dysfunction, this sympathetically activated blood volume recruitment may shift blood volume out of the splanchnic vessels to the central vascular system and may increase effective circulating blood volume, leading to potential increases in preload in the absence of any changes in the total body fluid volume (e.g., no change in body weight). This increase in preload (e.g., cardiac filling pressure) in some patients may cause AHF and the hospitalization.

It may be beneficial to provide systems and methods that can be used to determine whether acute heart failure, or acute decompensated heart failure (ADHF), is caused more by fluid accumulation or by fluid redistribution and to provide the appropriate treatment. In some cases, it may be beneficial to provide a clinical technique to provide a differential diagnosis as to whether AHF is mainly due to fluid accumulation (e.g., overall fluid gain) or fluid redistribution (e.g., volume shift from venous system to central circulation). For example, if the fluid accumulation is associated with increased volume, then diuretic therapy maybe appropriate. However, if volume overload is associated with a fluid shift, then diuretic therapy may not be appropriate and other treatment such as adrenergic blockade or other therapies may be prescribed.

The present disclosure provides a technique that may include determining whether a patient has cardiac volume overload, determining whether the patient has decreased abdominal venous system volume, and providing the appropriate treatment in response to the determinations. In some embodiments, both determinations may be made before providing treatment for acute heart failure. In other words, the determination for providing appropriate treatment may be made based on, in response to, or after determining whether the patient has cardiac volume overload and determining whether the patient has decreased abdominal venous system volume. A multi-sensor system may be used to carry out this technique. Providing the appropriate treatment for these two different conditions may facilitate providing effective treatment and the improvement of outcomes for some patients.

Reference will now be made to the drawings, which depict one or more aspects described in this disclosure. However, it will be understood that other aspects not depicted in the drawings fall within the scope of this disclosure. Like numbers used in the figures refer to like components, steps, and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

FIG. 1 shows a system 100 for acute heart failure monitoring and treatment. In general, system 100 is a multiple-sensor system. The system 100 may include one or more thoracic cardiac volume sensors 102 (also referred to as thoracic sensors or cardiac volume sensors), one or more abdominal venous system volume sensors 104 (also referred to as abdominal sensors or venous system volume sensors), a controller 106, and one or more user interface devices 108.

The thoracic sensor 102 may be configured to measure cardiac volume to detect volume overload conditions. The thoracic sensor 102 may be positioned in, on, or proximate to the patient's thorax. In some embodiments, the thoracic sensor 102 may be described as being, or being part of, a thoracic device.

The thoracic sensor 102 may be any suitable type of sensor for measuring cardiac volume. In some embodiments, the thoracic sensor 102 may use impedance, pressure, or weight to determine cardiac volume. Non-limiting examples of sensors of thoracic devices include: a thoracic sensor, a subcutaneous sensor, an intravascular sensor, a left-ventricular pressure sensor, a thoracic vascular-pressure sensor, an intrathoracic impedance sensor, and a weigh scale.

A thoracic vascular-pressure sensor, such as a pulmonary artery pressure sensor, for example, using estimated pulmonary arterial diastolic pressure (ePAD), may be used to monitor the level of cardiac filling pressure or hemodynamic status. In some embodiments, a thoracic vascular-pressure sensor may be placed in a chamber of the patient's heart or a blood vessel. Various examples of pulmonary artery pressure sensors are described in, for example, U.S. Pat. No. 6,887,207, issued May 3, 2005, entitled "Methods and apparatus for estimation of ventricular afterload based on ventricular pressure measurements," or U.S. patent Application No. 15/846,797, filed Dec. 19, 2017, entitled "Delivery catheter for implantable medical device," each of which is incorporated herein by reference in its entirety. One example of a pulmonary artery pressure sensor is an implantable hemodynamic monitor (IHM).

An intrathoracic impedance sensor may be used to monitor the level of or changes in thoracic volume, cardiac filling pressure, or hemodynamic status.

The abdominal sensor 104 may be configured to measure abdominal venous system volume, for example, to detect venous volume change. The abdominal sensor 104 may be positioned in, on, or proximate to the patient's abdomen, below the patient's thorax, or below the thoracic sensor 102. In some embodiments, the abdominal sensor 104 may be described as being, or being part of, an abdominal device.

The abdominal sensor 104 may be any suitable type of sensor for measuring abdominal venous system volume. Non-limiting examples of sensors of abdominal devices include: an abdominal sensor, an impedance monitor, an external patch monitor, a tissue oxygenation sensor, a dielectric-constant sensor, and a weight balance scale.

A balance scale, such as a bed scale, may be used to measure the relative weight of the patient's thorax versus the patient's abdomen, for example, when the patient is lying down. The relative weight, or ratio of weight, between the thorax and the abdomen may change as blood volume is redistributed to and from the abdominal venous system.

An impedance monitor may be used to measure bio-impedance. In general, as fluid level in the venous system (e.g., splanchnic bed) goes down, bio-impedance increases, and vice versa. For example, a Medtronic Reveal LINQ Insertable Cardiac Monitoring System may be placed near the patient's spleen to monitor venous system volume changes via impedance changes. As another example, an external patch monitor may be used to measure bio-impedance of the venous system (e.g., splanchnic region).

A tissue oxygenation sensor, such as a pulse oximeter, may be used to monitor changes in hemoglobin content. In some embodiments, the tissue oxygenation sensor may be placed near the patient's spleen.

A radio-frequency (RF) transmitter/receiver, for example, using a radar-like technique, may be used to measure one or more dielectric constants of one or more splanchnic organs. Changes in dielectric constants may indicate fluid volume change in the area.

The controller 106 may be operably coupled to the thoracic sensor 102, the abdominal sensor 104, or both the thoracic sensor 102 and the abdominal sensor 104. The controller 106 may be configured to determine whether a patient has cardiac volume overload in response to a cardiac volume measurement, for example, from the thoracic sensor 102. The controller 106 may be configured to determine whether a patient has a decreased abdominal venous system volume in response to an abdominal venous system volume measurement, for example, from the abdominal sensor 104. In some embodiments, the controller 106 may determine an appropriate treatment based on determining whether the patient has cardiac volume overload and determining whether the patient has decreased abdominal venous system volume.

In some embodiments, the controller 106 may be configured to provide fluid redistribution treatment in response to the patient having a cardiac volume overload and a decreased abdominal venous system volume. In some embodiments, the controller 106 may be configured to provide fluid accumulation treatment in response to determining that the patient has a cardiac volume overload and that the abdominal venous system volume of the patient has not decreased. For example, an implantable medical device implanted in the thorax of the patient (e.g., a thoracic device) may be used to provide the fluid accumulation treatment. The implantable medical device may include one or more thoracic sensors 102.

In the illustrated embodiment, the system 100 includes a first interface 110 to operably couple the controller 106 to the one or more thoracic sensors 102, a second interface 112 to operably couple the controller to the one or more abdominal sensors 104, and a third interface 114 to operably couple the controller to the one or more user interface devices 108. In some embodiments, the first interface 110, the second interface 112, or the third interface 114 may be described as being part of the controller 106.

The controller 106 may receive cardiac volume measurements from the first interface 110. The controller 106 may receive abdominal venous system volume measurements from the second interface 112. The controller 106 may provide measurements of the cardiac volume and the abdominal venous system volume to the third interface 114 or may receive commands or other information from the third interface.

In some embodiments, the first interface 110 may be operably coupled to two or more sensors to measure cardiac volume. Each of the sensors for measuring cardiac volume may be housed in the same thoracic device or different thoracic devices. In some embodiments, the second interface 112 may be operably coupled to two or more sensors to abdominal venous system volume. Each of the sensors for measuring abdominal venous system volume may be housed in the same abdominal device or different abdominal devices.

Each of the interfaces may use any suitable type of connection to operably connect the controller 106 with the sensors. For example, the connection may be electrical, optical, mechanical, wired, wireless, or any combination of these.

The user interface device 108 may include any suitable device capable of providing information to the user, receiving input from the user, or otherwise physically interacting with the user. In some embodiments, the user interface device 108 may be part of, or include, a desktop computer, a display, a touchscreen, a tablet, a smartphone, or other suitable device.

The user interface device 108 may receive measurements of the cardiac volume, the abdominal venous system volume, or both from the sensors 102, 104 via controller 106. The measurement information may be provided to a clinician for diagnosis, for example, using a display.

In some cases, the user interface device 108 may receive measurements of the cardiac volume, abdominal venous system volume, or both from user input. For example, a patient may be weighed on a weight balance scale or weigh scale to provide cardiac volume or abdominal venous system volume information to a clinician who may input the information into the user interface device 108 for use by the controller 106. For example, the controller 106 may compare the inputted information to information from one or more sensors or from a database of user information. The controller 106 may determine whether to provide fluid accumulation treatment or fluid redistribution treatment based on the user input, the sensor information, or both.

One or more of the components, such as controllers, interfaces, or sensors, described herein may include a processor, such as a central processing unit (CPU), computer, logic array, or other device capable of directing data coming into or out of devices. The controller may include one or more computing devices having memory, processing, and communication hardware. The controller may include circuitry used to couple various components of the controller together or with other components operably coupled to the controller. The functions of the controller may be performed by hardware and/or as computer instructions on a non-transient computer readable storage medium.

The processor of the controller may include any one or more of a microprocessor, a microcontroller, a digital signal processor (DSP), an application specific integrated circuit (ASIC), a field-programmable gate array (FPGA), and/or equivalent discrete or integrated logic circuitry. In some examples, the processor may include multiple components, such as any combination of one or more microprocessors, one or more controllers, one or more DSPs, one or more ASICs, and/or one or more FPGAs, as well as other discrete or integrated logic circuitry. The functions attributed to the controller or processor herein may be embodied as software, firmware, hardware, or any combination thereof. While described herein as a processor-based system, an alternative controller could utilize other components such as relays and timers to achieve the desired results, either alone or in combination with a microprocessor-based system.

In one or more embodiments, the exemplary systems, methods, and interfaces may be implemented using one or more computer programs using a computing apparatus, which may include one or more processors and/or memory. Program code and/or logic described herein may be applied to input data/information to perform functionality described herein and generate desired output data/information. The output data/information may be applied as an input to one or more other devices and/or methods as described herein or as would be applied in a known fashion. In view of the above, it will be readily apparent that the controller functionality as described herein may be implemented in any manner known to one skilled in the art.

Figure 2:
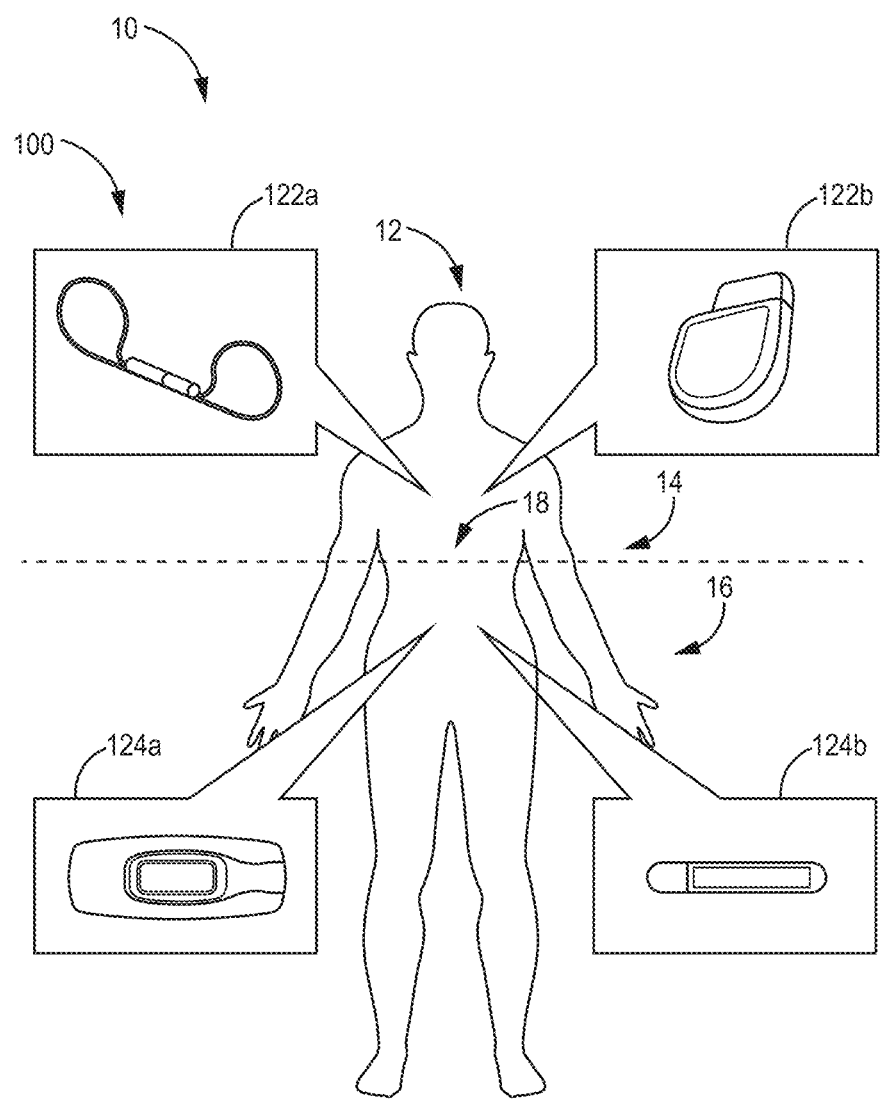
FIG. 2 is a diagram that illustrates a patient and sensor devices for use in the system of FIG. 1 according to the present disclosure.

FIG. 2 shows an environment 10 including a patient 12 and the AHF monitoring and treatment system 100. The system 100 may include various sensor devices, such as sensor devices 122a, 122b, 124a, and 124c, to measure fluid volumes within the patient 12. In the illustrated embodiment, certain sensor devices 122a, 122b (collectively referred to as, thoracic devices 122) may be positioned in, on, or near the thorax 14 of the patient. Other sensor devices 124a, 124b (collectively referred to as abdominal devices 124) may be positioned in, on, or near the abdomen 16 of the patient. Although four sensor devices are shown, the system 100 generally includes at least one thoracic device and at least one abdominal device.

As used herein, the term "thorax" refers to the part of the patient's body that is within or covered by the ribcage, above a lowest or most inferior point 18 of the patient's ribcage, or both. The lowest or most inferior point may be aligned to a plane that is orthogonal to the caudocranial axis of the patient. The thorax may be defined as the part of the patient's body above the plane and below the patient's neck. Being on or proximate to the patient's thorax may include, for example, being on the patient's clavicle, between the shoulder blades, or inside the mesenteric vein.

As used herein, the term "abdominal" refers to the part of the patient's body that is below the thorax, below a lowest or most inferior point 18 of the patient's ribcage, or both. The abdomen may be defined as the part of the patient's body above the legs and below the thorax. The abdomen may include one or more splanchnic organs, such as the spleen, the liver, one or two kidneys, and the intestine.

Each of the thoracic devices 122 and abdominal devices 124 may include one or more sensors for detecting fluid volume. For example, each thoracic device 122 may house, or include, one or more thoracic sensors 102 (FIG. 1). More than one thoracic sensor 102 may be used in each thoracic device 122, for example, to provide redundant measurements. More than one thoracic device 122 may also be used to provide redundant measurements. The additional thoracic sensors 102 may use a different type of sensing, or sensing mechanism, to measure cardiac volume. The redundant measurements may facilitate reporting a more accurate measurement of abdominal venous system volume, for example, to verify a measurement or to average measurements.

Each abdominal device 124 may house, or include, one or more abdominal sensors 104 (FIG. 1). More than one abdominal sensor 104 may be used in each abdominal device 124, for example, to provide redundant measurements. More than one abdominal device 124 may also be used to provide redundant measurements. The additional abdominal sensors 104 may use a different type of sensing, or sensing mechanism, to measure abdominal venous system volume. The redundant measurements may facilitate reporting a more accurate measurement of abdominal venous system volume, for example, to verify a measurement or to average measurements.

Being positioned in, on, or proximate to the patient's thorax or abdomen may include being internal, external, or both. In some embodiments, one or more sensors 102, 104 (FIG. 1) or devices 122, 124 may be implanted subcutaneously for ambulatory and continuous monitoring (e.g., when using an impedance sensor). In some embodiments, one or more sensors 102, 104 or devices 122, 124 may be implanted in the patient's heart or blood vessels. In some embodiments, one or more sensors 102, 104 or devices 122, 124 may be positioned externally for temporary or confirmatory monitoring (e.g., when using a patch monitor).

In various embodiments, parts of the devices (e.g., housings having a controller) 122, 124 may be positioned on a different part of the patient's body. Those parts of the devices 122, 124 may be operably connected to one or more sensors 102, 104, for example, by a lead, wireless communication, or any other suitable interface.

In general, thoracic sensors 102 of thoracic devices 122 may be positioned closer to the patient's heart than abdominal sensors 104 of abdominal devices 124. In some embodiments, thoracic sensors 102 may be positioned in or proximate to the patient's heart, which may provide for more accurate measurements of cardiac volume.

One or more of the sensor devices 122, 124 may include a controller, such as controller 106 (FIG. 1). The controller may be operably coupled to one or more sensors from the same sensor device or other sensor devices. Some examples of sensor devices include: intracardiac or intravascular pressure sensors, subcutaneous sensors, impedance monitoring systems (e.g., Medtronic OptiVol used with implantable pulse generator (IPG), implantable cardioverter-defibrillator (ICD), or cardiac resynchronization therapy (CRT) device), external patch-like devices with impedance monitoring features, implantable loop recorders with optical sensors and/or impedance sensors (e.g., Reveal LinQ), implantable flow sensors, tissue-oxygenation sensors, dielectric constant sensors, weigh scales or weight balance scales, or other suitable sensor devices.

The sensor device 122*a* may use a different type of sensing than the sensor device 122*b*, and the sensor device 124*a* may use a different type of sensing than the sensor device 124*b*. In the illustrated embodiment, the sensor device 122*a* is an intracardiac or intravascular pressure sensor, the sensor device 122*b* is an implantable medical device (e.g., IPG, ICD, or CRT device) that uses an impedance sensor, the sensor device 124*a* is a patch-like device that uses an external local impedance sensor, and the sensor device 124*b* is a loop recorder (e.g., Medtronic Reveal LinQ) that uses an implantable pressure sensor.

In some embodiments, one or more sensor devices 122, 124 may be used to provide treatment, such as fluid accumulation treatment or fluid redistribution treatment. The sensor devices 122, 124 may cooperatively provide a closed loop system for monitoring cardiac volume and abdominal venous system volume and to provide the appropriate treatment.

Figure 3:
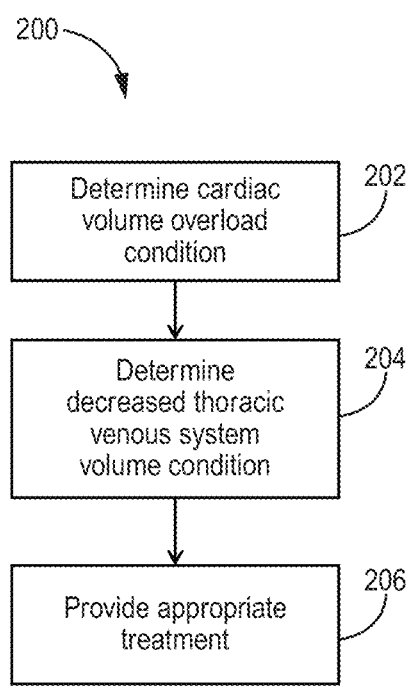
FIG. 3 is a flow diagram that illustrates a method for acute heart failure monitoring and treatment according to the present disclosure.

FIG. 3 shows a method 200 for acute heart failure monitoring and treatment. The method 200 may include determining a cardiac volume overload condition 202. One or more thoracic devices, each having one or more cardiac volume sensors, may be used to measure the cardiac volume of the patient. A cardiac volume overload condition may be determined based on one or more measurements of cardiac volume. The method 200 may also include determining a decreased thoracic venous system volume condition 204. One or more abdominal devices, each having one or more abdominal venous system volume sensors, may be used to measure the abdominal venous system volume of the patient. A decreased abdominal venous system volume condition may be determined based on one or more measurements of the abdominal venous system volume. The method 200 may include providing appropriate treatment 206 based on the cardiac volume overload condition and the decreased thoracic venous system volume condition. One or more thoracic devices or abdominal devices may be configured to provide fluid accumulation treatment or fluid redistribution treatment. In some embodiments, information may be provided to a user interface device to facilitate a clinician's decision regarding whether to provide fluid accumulation treatment or fluid redistribution treatment.

Various techniques may be used to determine whether the patient has cardiac overload or a decreased thoracic venous system volume. In some embodiments, the cardiac volume measurement may be compared to a fixed value threshold. If the measurement exceeds the threshold, then cardiac overload may be determined. In some embodiments, cumulative, or accumulated, cardiac volume measurements may be compared to a cumulative, or accumulated, threshold. Various techniques for using an accumulated threshold are described in U.S. Pat. No. 7,986,994, issued Jul. 26, 2011, entitled "Method and apparatus for detecting change in intrathoracic electrical impedance," which is incorporated by reference in its entirety.

In some embodiments, if a change in abdominal venous system volume is greater than a change in cardiac volume, for example, compared to respective baseline values, then fluid redistribution treatment may be provided. Otherwise, fluid accumulation treatment may be provided.

Figure 4:
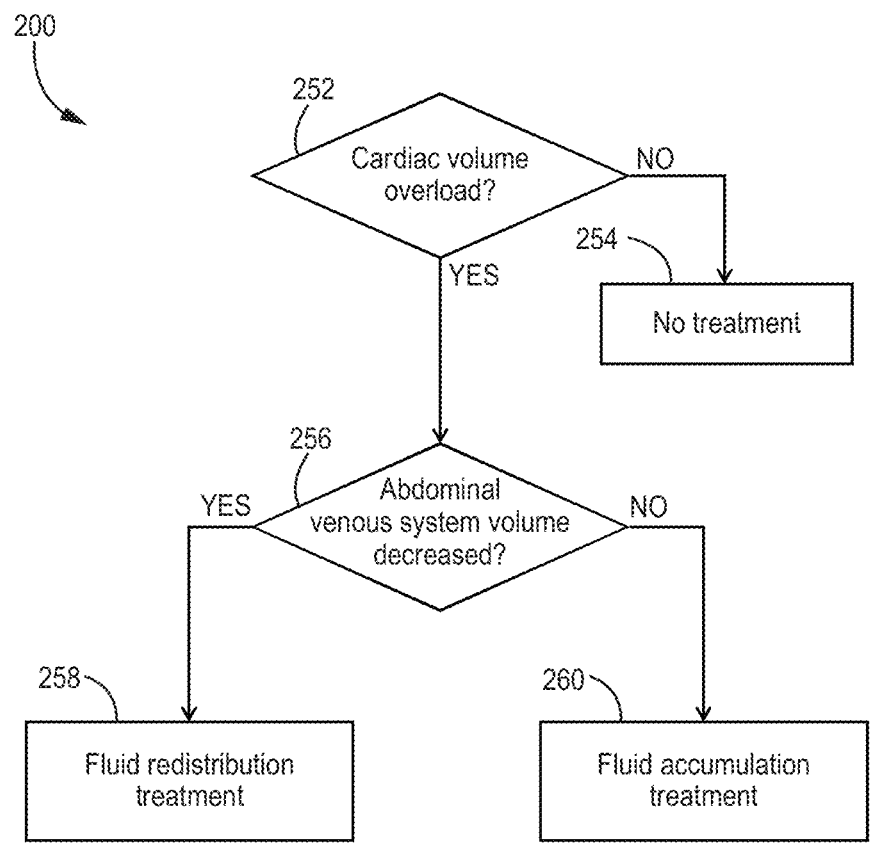
FIG. 4 is a flow diagram that illustrates one method for carrying out the method of FIG. 3 according to the present disclosure.

FIG. 4 shows a method 250 for carrying out the method 200 (FIG. 3) for acute heart failure monitoring and treatment. Method 252 may include determining whether there is a cardiac volume overload. If there is no cardiac volume overload, then no treatment may be provided 254. If there is cardiac volume overload, for example, more than a threshold value, the method 250 may continue to check abdominal venous system volume.

Method 250 may include determining whether abdominal venous system volume has decreased 256. If abdominal venous system volume has decreased, for example, more than a threshold value, the method 250 may include providing fluid redistribution treatment 258 (e.g., administering drug). If abdominal venous system volume has not decreased, the method 250 may include providing fluid accumulation treatment 260 (e.g., diuresis).

Fluid redistribution treatment may include any suitable treatment that moves fluid from the cardiac volume to the abdominal venous system volume. In some embodiments, fluid redistribution treatment may involve activation of the sympathetic nerve stimuli, administering drugs, or administering hormones. Non-limiting examples of fluid redistribution treatment include using or increasing adrenergic blockade (e.g., combined alpha and beta blockers), providing instructions for bed rest (e.g., avoid an upright posture), and providing instructions for breathing therapy (e.g., to counter an elevated sympathetic tone). Breathing therapy may facilitate an increase in abdominal capacity.

Fluid accumulation treatment may include any suitable treatment that reduces the overall fluid in the vascular system or more specifically reduces the fluid in the cardiac volume. Non-limiting examples of fluid accumulation treatment include increasing diuretic dosage, administering plasmapheresis, and controlling a therapy device to provide fluid accumulation treatment. For example, a cardiac resynchronization therapy (CRT) device or a ventricular assist device, such as a left ventricular assist device (LVAD), may be used to modulate the rate of pacing, pacing delay values, or pacing modes to facilitate a reduction in fluid.

Figure 5:
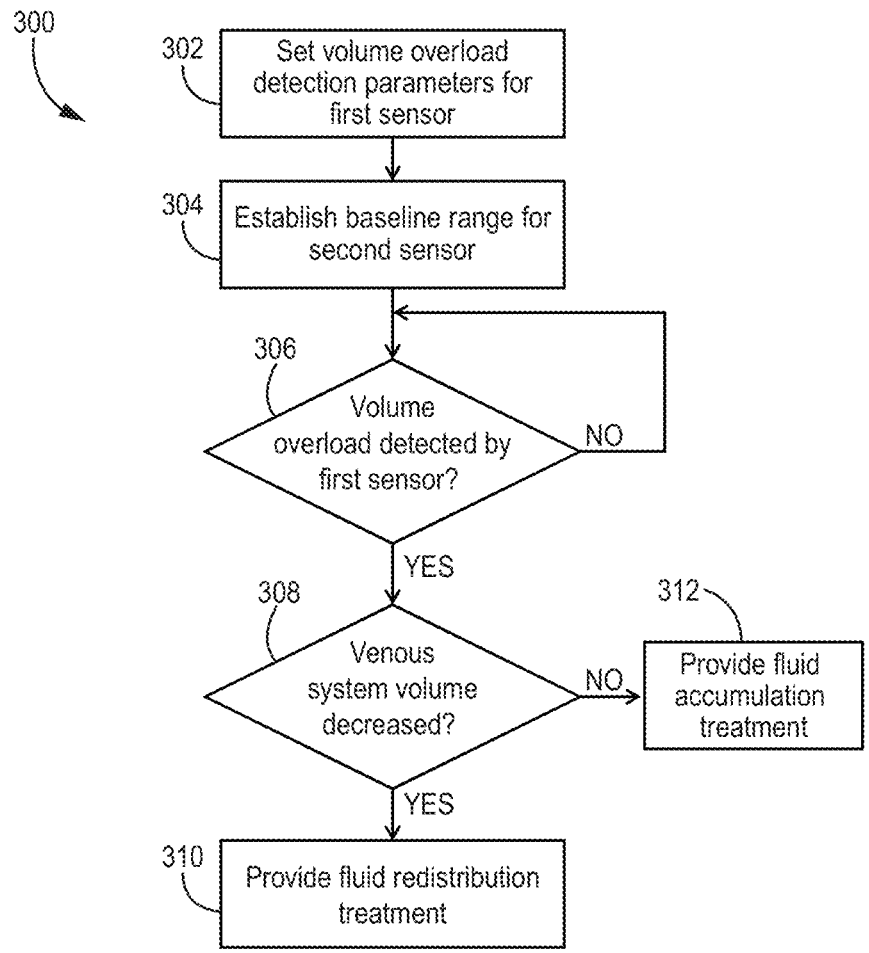
FIG. 5 is a flow diagram that illustrates another method for carrying out the method of FIG. 3 according to the present disclosure.

FIG. 5 shows another method 300 for carrying out the method 200 (FIG. 3) for acute heart failure monitoring and treatment. In general, the method 300 may monitor a first sensor for detection of volume overload. Once detected, a second sensor may be activated, or cross-referenced if continuous or periodic measurements are used, to determine whether the abdominal venous system volume (e.g., splanchnic volume) has been decreased or has decreased. If the abdominal venous system volume has changed beyond a pre-specified threshold, or shows a decreasing trend from multiple measurements, then the volume overload detected by the first sensor may be determined to be due to fluid volume redistribution rather than overall fluid volume accumulation.

In some embodiments, the accuracy of the volume measurements may depend on the patient's posture. A patient may be restricted in movement or may be instructed to maintain a consistent posture as the one or more measurements are being taken, particularly for multiple measurements being taken over time.

The method 300 may include setting a volume overload detection parameter (e.g., threshold) for a first sensor (e.g., cardiac volume sensor) 302. For example, cardiac pressure may be measured as a representation of cardiac volume, and when the pulmonary arterial pressure exceeds 28 mmHg, then cardiac overload may be determined. The method 300 may include establishing a baseline range for a second sensor (e.g., abdominal venous system volume sensor) 304. For example, a subcutaneous impedance near the splanchnic bed may be measured for a baseline value.

The method 300 may further include determining whether volume overload has been detected by the first sensor 306. If volume overload has not been detected, the method 300 may continue to monitor for volume overload. If volume overload has been detected, the method 300 may check venous system volume.

The method 300 may include determining whether venous system volume (e.g., splanchnic volume) has decreased 308. If venous system volume has decreased, the method 300 may include providing fluid redistribution treatment 310. Otherwise, if venous system volume has not decreased, the method 300 may include providing fluid accumulation treatment 312.

While the present disclosure is not so limited, an appreciation of various aspects of the disclosure will be gained through a discussion of the illustrative embodiments provided below. Various modifications of the illustrative embodiments, as well as additional embodiments of the disclosure, will become apparent herein.

ILLUSTRATIVE EMBODIMENTS

In illustrative embodiment A1, a method comprises determining whether a patient has cardiac volume overload; determining whether a patient has decreased abdominal venous system volume; and determining an appropriate based on determining whether the patient has cardiac volume overload and determining whether the patient has decreased abdominal venous system volume.

In illustrative embodiment A2, a method comprises a method as in any A embodiment, further comprising providing fluid redistribution treatment in response to determining that the patient has a cardiac volume overload and a decreased abdominal venous system volume.

In illustrative embodiment A3, a method comprises a method as in any A embodiment, further comprising providing fluid accumulation treatment in response to determining that the patient has a cardiac volume overload and that the abdominal venous system volume of the patient has not decreased.

In illustrative embodiment A4, a method comprises a method as in any A embodiment, wherein one or both of cardiac volume overload and decreased abdominal venous system volume of the patient is determined based on a fixed value threshold or a cumulative value threshold.

In illustrative embodiment A5, a method comprises a method as in any A embodiment, wherein determining that the patient has cardiac volume overload comprises using a cardiac volume sensor positioned in, on, or proximate to the patient's thorax.

In illustrative embodiment A6, a method comprises a method as in embodiment A5, wherein the cardiac volume sensor is positioned in or proximate to the patient's heart.

In illustrative embodiment A7, a method comprises a method as in embodiment A5 or A6, wherein the cardiac volume sensor comprises one or more of: a thoracic sensor, a subcutaneous sensor, an intravascular sensor, a left-ventricular pressure sensor, a thoracic vascular-pressure sensor, an intrathoracic impedance sensor, and a weigh scale.

In illustrative embodiment A8, a method comprises a method as in any A embodiment, wherein determining whether the patient has decreased abdominal venous system volume comprises using a venous system volume sensor positioned in, on, or proximate to the patient's abdomen.

In illustrative embodiment A9, a method comprises a method as in embodiment A8, wherein the venous system volume sensor is positioned at or proximate to one or more of: a splanchnic organ, a spleen, a liver, a kidney, and an intestine.

In illustrative embodiment A10, a method comprises a method as in embodiment A8 or A9, wherein the venous system volume sensor comprises one or more of: an abdominal sensor, an impedance monitor, an external patch monitor, a tissue oxygenation sensor, a dielectric-constant sensor, and a weight balance scale.

In illustrative embodiment A11, a method comprises a method as in any A embodiment, wherein providing fluid redistribution treatment comprises one or more of: using or increasing adrenergic blockade, providing instructions for bed rest, and providing instructions for breathing therapy.

In illustrative embodiment A12, a method comprises a method as in any embodiment A3-A11, wherein providing fluid accumulation treatment comprises one or more of increasing diuretic dosage and administering plasmapheresis.

In illustrative embodiment A13, a method comprises a method as in embodiment A12, further comprising controlling a therapy device to provide the fluid accumulation treatment.

In illustrative embodiment B1, a system comprises: one or both of a thoracic device comprising a sensor to measure cardiac volume and an abdominal device comprising a sensor to measure abdominal venous system volume; and a controller operably coupled to the thoracic device or the abdominal device. The controller comprises a processor configured to: determine whether a patient has cardiac volume overload in response to a cardiac volume measurement; determine whether a patient has decreased abdominal venous system volume in response to an abdominal venous system volume measurement; and determine an appropriate treatment based on determining whether the patient has cardiac volume overload and determining whether the patient has decreased abdominal venous system volume.

In illustrative embodiment B2, a system comprises a system as in any B embodiment, wherein the processor is further configured to: provide fluid redistribution treatment in response to determining that the patient has a cardiac volume overload and a decreased abdominal venous system volume; or provide fluid accumulation treatment in response to the patient has a cardiac volume overload and that the abdominal venous system volume of the patient has not decreased.

In illustrative embodiment B3, a system comprises a system as in any B embodiment, further comprising another sensor to measure cardiac volume.

In illustrative embodiment B4, a system comprises a system as in embodiment B3, wherein each sensor to measure cardiac volume uses a different type of sensing to measure cardiac volume.

In illustrative embodiment B5, a system comprises a system as in any B embodiment, further comprising another sensor to measure abdominal venous system volume.

In illustrative embodiment B6, a system comprises a system as in embodiment B5, wherein each sensor to measure abdominal venous system volume uses a different type of sensing to measure abdominal venous system volume.

In illustrative embodiment B7, a system comprises a system as in any B embodiment, wherein the sensor of the thoracic device positioned in, on, or proximate to the patient's thorax.

In illustrative embodiment B8, a system comprises a system as in any B embodiment, wherein the sensor of the thoracic device is positioned in or proximate to the patient's heart.

In illustrative embodiment B9, a system comprises a system as in any B embodiment, wherein the sensor of the thoracic device comprises at least one of: a thoracic sensor, a subcutaneous sensor, an intravascular sensor, a left-ventricular pressure sensor, a thoracic vascular-pressure sensor, an intrathoracic impedance sensor, and a weigh scale.

In illustrative embodiment B10, a system comprises a system as in any B embodiment, wherein the sensor of the abdominal device is positioned in, on, or proximate to the patient below the sensor of the thoracic device and below the thorax of the patient.

In illustrative embodiment B11, a system comprises a system as in any B embodiment, wherein the sensor of the abdominal device is positioned at or proximate to at least one of: a splanchnic organ, a spleen, a liver, a kidney, and an intestine.

In illustrative embodiment B12, a system comprises a system as in any B embodiment, wherein the sensor of the abdominal device comprises at least one of: an abdominal sensor, an impedance monitor, an external patch monitor, a tissue oxygenation sensor, a dielectric-constant sensor, and a weight balance scale.

In illustrative embodiment C1, a system comprises: an interface to one or more thoracic devices to measure cardiac volume; an interface to one or more abdominal devices to measure abdominal venous system volume; an interface to one or more user interface devices; and a controller operably coupled to the interfaces to one or more thoracic devices and to one or more abdominal devices to receive measurements of cardiac volume and abdominal venous system volume. The controller comprises a processor configured to: receive a cardiac volume using the interface to one or more thoracic devices; receive an abdominal venous system volume using the interface to one or more abdominal devices; and provide measurements of the cardiac volume and the abdominal venous system volume using the interface to one or more user interface devices.

In illustrative embodiment C2, a system comprises a system as in any C embodiment, further comprising an implantable medical device configured to provide fluid accumulation treatment in response to determining that a patient has a cardiac volume overload and that the abdominal venous system volume of the patient has not decreased.

In illustrative embodiment C3, a system comprises a system as in any C embodiment, wherein the controller is further configured to determine an appropriate treatment based on determining whether the patient has cardiac volume overload and determining whether the patient has decreased abdominal venous system volume.

In illustrative embodiment C4, a system comprises a system as in any C embodiment, wherein the interface to one or more thoracic devices is operably coupled to two or more sensors to measure cardiac volume, the interface to one or more abdominal devices is operably coupled to two or more sensors to measure abdominal venous system volume, or both.

Thus, various embodiments of ACUTE HEART FAILURE MONITORING AND TREATMENT are disclosed. Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be understood that each block of the block diagrams and combinations of those blocks can be implemented by means for performing the illustrated function.

All references and publications cited herein are expressly incorporated herein by reference in their entirety for all purposes, except to the extent any aspect directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality.

Terms related to orientation, such as "above" and "below" are used to describe relative positions of components and are not meant to limit the orientation of the embodiments contemplated.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

The term "and/or" means one or all of the listed elements or a combination of at least two of the listed elements.

The phrases "at least one of," "comprises at least one of," and "one or more of" followed by a list refers to any one of the items in the list and any combination of two or more items in the list.

What is claimed is:

1. A method comprising:
   determining, using a controller, whether a patient has cardiac volume overload based on a measured cardiac volume;
   determining, using the controller, whether the patient has decreased abdominal venous system volume based on a measured abdominal venous system volume; and
   determining, using the controller, an appropriate treatment based on determining whether the patient has cardiac volume overload and determining whether the patient has decreased abdominal venous system volume, wherein the appropriate treatment comprises fluid accumulation treatment when the patient has cardiac volume overload and does not have decreased abdominal venous system volume, wherein the fluid accumulation treatment comprises one or more of increasing diuretic dosage and administering plasmapheresis.

2. A method as in claim 1, wherein the appropriate treatment comprises fluid redistribution treatment when the patient has cardiac volume overload and decreased abdominal venous system volume.

3. A method as in claim 1, wherein one or both of cardiac volume overload and decreased abdominal venous system volume of the patient is determined by comparing one or both of the measured cardiac volume and measured abdominal venous system volume to a fixed value threshold or a cumulative value threshold.

4. A method as in claim 2, wherein the fluid redistribution treatment comprises one or more of: using or increasing adrenergic blockade, providing instructions for bed rest, and providing instructions for breathing therapy.

5. A method as in claim 1, further comprising controlling a therapy device to provide the fluid accumulation treatment.

6. A system comprising:
a thoracic device comprising a sensor to measure cardiac volume;
an abdominal device comprising a sensor to measure abdominal venous system volume; and
a controller operably coupled to the thoracic device and the abdominal device, the controller comprising a processor configured to:
determine whether a patient has cardiac volume overload in response to a cardiac volume measurement;
determine whether the patient has decreased abdominal venous system volume in response to an abdominal venous system volume measurement; and
determine an appropriate treatment based on determining whether the patient has cardiac volume overload and determining whether the patient has decreased abdominal venous system volume, wherein the appropriate treatment comprises fluid accumulation treatment when the patient has cardiac volume overload and does not have decreased abdominal venous system volume, wherein the fluid accumulation treatment comprises one or more of increasing diuretic dosage and administering plasmapheresis.

7. A system as in claim 6, wherein the appropriate treatment comprises
fluid redistribution treatment when the patient has a cardiac volume overload and a decreased abdominal venous system volume.

8. A system as in claim 6, further comprising another sensor to measure cardiac volume.

9. A system as in claim 8, wherein each sensor to measure cardiac volume uses a different type of sensing to measure cardiac volume.

10. A system as in claim 6, further comprising another sensor to measure abdominal venous system volume.

11. A system as in claim 10, wherein each sensor to measure abdominal venous system volume uses a different type of sensing to measure abdominal venous system volume.

12. A system as in claim 6, wherein the sensor of the thoracic device is positioned in, on, or proximate to the patient's thorax.

13. A system as in claim 6, wherein the sensor of the thoracic device is positioned in or proximate to the patient's heart.

14. A system as in claim 6, wherein the sensor of the thoracic device comprises at least one of: a thoracic sensor, a subcutaneous sensor, an intravascular sensor, a left-ventricular pressure sensor, a thoracic vascular-pressure sensor, an intrathoracic impedance sensor, and a weigh scale.

15. A system as in claim 6, wherein the sensor of the abdominal device is positioned in, on, or proximate to the patient below the sensor of the thoracic device and below the thorax of the patient.

16. A system as in claim 6, wherein the sensor of the abdominal device is positioned at or proximate to at least one of: a splanchnic organ, a spleen, a liver, a kidney, and an intestine.

17. A system as in claim 6, wherein the sensor of the abdominal device comprises at least one of: an abdominal sensor, an impedance monitor, an external patch monitor, a tissue oxygenation sensor, a dielectric-constant sensor, and a weight balance scale.

18. A system comprising:
an interface to one or more thoracic devices to measure cardiac volume;
an interface to one or more abdominal devices to measure abdominal venous system volume;
an interface to one or more user interface devices; and
a controller operably coupled to the interfaces to one or more thoracic devices and to one or more abdominal devices to receive measurements of cardiac volume and abdominal venous system volume, the controller comprising a processor configured to:
receive a cardiac volume using the interface to one or more thoracic devices;
receive an abdominal venous system volume using the interface to one or more abdominal devices; and
determine an appropriate treatment based on whether the patient has a cardiac volume overload and whether the patient has decreased abdominal venous system volume, wherein the appropriate treatment comprises fluid accumulation treatment when the patient has cardiac volume overload and does not have decreased abdominal venous system volume, wherein the fluid accumulation treatment comprises one or more of increasing diuretic dosage and administering plasmapheresis.

19. A system as in claim 18, further comprising an implantable medical device configured to provide fluid accumulation treatment in response to determining that a patient has a cardiac volume overload and determining that the abdominal venous system volume of the patient has not decreased.

20. A system as in claim 18, wherein the interface to one or more thoracic devices is operably coupled to two or more sensors to measure cardiac volume, the interface to one or more abdominal devices is operably coupled to two or more sensors to measure abdominal venous system volume, or both.

21. A system as in claim 18, wherein the appropriate treatment comprises fluid redistribution treatment when the patient has a cardiac volume overload and a decreased abdominal venous system volume.

* * * * *